United States Patent
van Hal et al.

(10) Patent No.: US 9,458,715 B2
(45) Date of Patent: Oct. 4, 2016

(54) DETERMINING THE PLUS FRACTION OF A GAS CHROMATOGRAM

(71) Applicant: Schlumberger Technology Corporation, Sugar Land, TX (US)

(72) Inventors: Ronald E. G. van Hal, Belmont, MA (US); Jeffrey Crank, Walpole, MA (US); Youxiang Zuo, Burnaby (CA); Adriaan Gisolf, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 134 days.

(21) Appl. No.: 14/572,724

(22) Filed: Dec. 16, 2014

(65) Prior Publication Data

US 2016/0168990 A1   Jun. 16, 2016

(51) Int. Cl.
| | |
|---|---|
| *G01N 33/28* | (2006.01) |
| *G01N 30/88* | (2006.01) |
| *E21B 49/08* | (2006.01) |
| *G01N 30/86* | (2006.01) |

(52) U.S. Cl.
CPC ......... *E21B 49/087* (2013.01); *G01N 30/8675* (2013.01)

(58) Field of Classification Search
CPC .................. G01N 2030/8854; G01N 33/2823; G01N 30/00; G01N 2030/009; G01N 33/241; G01N 33/28
See application file for complete search history.

(56) References Cited

U.S. PATENT DOCUMENTS

| | | | |
|---|---|---|---|
| 4,739,654 A | 4/1988 | Pilkington et al. | |
| 5,163,982 A * | 11/1992 | de Andrade Bruuning | G01N 33/2829 210/635 |
| 7,384,453 B2 | 6/2008 | Bostrom et al. | |
| 7,600,413 B2 | 10/2009 | Shah et al. | |
| 7,637,151 B2 | 12/2009 | Raghuraman et al. | |
| 7,654,130 B2 | 2/2010 | Shah et al. | |
| 7,658,092 B2 | 2/2010 | Bostrom et al. | |
| 7,805,979 B2 | 10/2010 | Reddy et al. | |
| 7,822,554 B2 | 10/2010 | Zuo et al. | |
| 7,920,970 B2 | 4/2011 | Zuo et al. | |
| 7,966,273 B2 | 6/2011 | Hegeman et al. | |
| 7,996,154 B2 | 8/2011 | Zuo et al. | |
| 8,013,295 B2 | 9/2011 | Zhdaneev et al. | |

(Continued)

FOREIGN PATENT DOCUMENTS

| | | | | |
|---|---|---|---|---|
| CA | EP 2863216 A1 * | 4/2015 | ............. | G01N 30/00 |
| GB | WO 2013121204 A3 * | 9/2014 | ........... | G06F 19/703 |

OTHER PUBLICATIONS

Duan et al. "Modeling the characterization of the plus fractions by using continuous distribution function," Fluid Phase Equilibria, 345, (2013), pp. 1-10.

(Continued)

*Primary Examiner* — David A Rogers
(74) *Attorney, Agent, or Firm* — David G. Matthews; Cathy Hewitt

(57) ABSTRACT

Methods and devices for determining a plus fraction of a plus fraction of a gas chromatogram are provided. A gas chromatogram may obtained, such as from a downhole gas chromatograph module of a fluid analysis tool. The plus fraction of the gas chromatogram may be determined using one or more of a ratiometric determination, fitting an exponential decay function, and fitting a probability density gamma function.

20 Claims, 8 Drawing Sheets

(56) References Cited

U.S. PATENT DOCUMENTS

| | | |
|---|---|---|
| 8,028,562 B2 | 10/2011 | Shah et al. |
| 8,250,904 B2 | 8/2012 | Shah et al. |
| 8,271,248 B2 | 9/2012 | Pomerantz et al. |
| 8,512,457 B2 | 8/2013 | Steinecker et al. |
| 8,522,600 B2 * | 9/2013 | Al-Eid ............... G01N 30/12 73/23.38 |
| 8,613,215 B2 | 12/2013 | Lambertus et al. |
| 8,621,912 B2 | 1/2014 | Guieze |
| 8,968,560 B2 * | 3/2015 | Steinecker ........... G01N 30/461 210/198.2 |
| 2008/0141767 A1 * | 6/2008 | Raghuraman ...... G01N 33/2823 73/152.55 |
| 2009/0139934 A1 | 6/2009 | Steinecker |
| 2009/0150087 A1 | 6/2009 | Steinecker |
| 2009/0158815 A1 | 6/2009 | Shah et al. |
| 2009/0158820 A1 | 6/2009 | Bostrom et al. |
| 2009/0312997 A1 | 12/2009 | Freed et al. |
| 2010/0018287 A1 | 1/2010 | Iakimov |
| 2010/0127163 A1 | 5/2010 | Zhdaneev et al. |
| 2010/0154511 A1 | 6/2010 | Lambertus et al. |
| 2010/0299078 A1 | 11/2010 | Guieze |
| 2011/0011156 A1 | 1/2011 | Guieze |
| 2011/0011157 A1 | 1/2011 | Bourlon et al. |
| 2011/0088895 A1 | 4/2011 | Pop et al. |
| 2012/0021529 A1 | 1/2012 | Nachef et al. |
| 2012/0048108 A1 | 3/2012 | Steinecker et al. |
| 2012/0085149 A1 * | 4/2012 | Al-Eid ............... G01N 30/12 73/23.41 |
| 2012/0232859 A1 | 9/2012 | Pomerantz et al. |
| 2012/0296617 A1 | 11/2012 | Zuo et al. |
| 2013/0085674 A1 | 4/2013 | Zhdaneev et al. |
| 2014/0260586 A1 | 9/2014 | van Hal et al. |
| 2015/0039241 A1 * | 2/2015 | Moorwood ........... G06F 19/703 702/24 |
| 2015/0112609 A1 * | 4/2015 | Hu ..................... G01N 30/00 702/24 |

OTHER PUBLICATIONS

Eckert et al. "Effective characterization of petroleum C7+ fractions," Fuel, vol. 102 (2012), pp. 545-553.

Gisolf, et al. "Real Time Integration of Reservoir Modeling and Formation Testing," SPE 121275, prepared for presentation at the 2009 SPE EUROPEC/EAGE Annual Conference and Exhibition held in Amsterdam, The Netherlands, Jun. 8-11, 2009, pp. 1-13.

Hoffmann, et al. "Equilibrium Constants for a Gas-Condensate System," SPE 219-G, Petroleum Transactions, AIME, T.P. 3493, vol. 198, (1953), pp. 1-10.

Hosein et al. "A four coefficient model for extending the heptanes-plus fraction for gas condensate systems," Journal of Petroleum Science and Engineering, 100 (2012), pp. 59-70.

Katz "Overview of Phase Behavior in Oil and Gas Production," SPE 9995, Journal of Petroleum Technology, vol. 35, Jun. 1983, pp. 1205-1214.

Mohamad, et al. "A generalized set of correlations for plus fraction characterization," Pet. Sci., (2012), vol. 9, pp. 370-378.

Rodriguez, et al. "An approach for characterization and lumping of plus fractions of heavy oil," SPE 117446, SPE Reservoir Evaluation & Engineering, Apr. 2010, pp. 283-295.

Whitson "Characterizing Hydrocarbon Plus Fractions," SPE 12233, Society of Petroleum Engineers Journal, vol. 23, Aug. 1983, pp. 683-694.

Zuo, et al. "Integration of Fluid Log Predictions and Downhole Fluid Analysis," SPE 122562, prepared for presentation at the 2009 SPE Asia Pacific Oil and Gas Conference and Exhibition held in Jakarta, Indonesia, Aug. 4-6, 2009, pp. 1-11.

* cited by examiner

DETERMINING THE PLUS FRACTION OF A GAS CHROMATOGRAM

BACKGROUND

This disclosure relates to fluid analysis and, more particularly, to quantifying components of a fluid using gas chromatography.

This disclosure relates to determination of fluid composition using downhole fluid analysis (DFA). The composition of a fluid may be determined from various measurements obtained from a fluid downhole in a well. However, composition determinations for a fluid downhole may be difficult and may not provide accurate measurements of all components of a fluid. Moreover, extracting a fluid sample to a surface laboratory to provide a detailed composition analysis may be time-consuming and may be insufficiently responsive for reservoir development, production, and management.

SUMMARY

A summary of certain embodiments disclosed herein is set forth below. It should be understood that these embodiments and associated aspects are presented merely to provide the reader with a brief summary of these certain embodiments and that these aspects are not intended to limit the scope of this disclosure. Indeed, this disclosure may encompass a variety of embodiments and aspects that may not be set forth below.

Embodiments of this disclosure relate to various systems, methods, and devices for determining the plus fraction of a gas chromatogram. In some embodiments, there is provided a method for analyzing a fluid having a plurality of components that includes obtaining a gas chromatogram of the fluid, the gas chromatogram having a plus fraction, and determining, from the gas chromatogram, a first ratio of a first at least one component of the fluid to a second at least one component of the fluid. The method further includes comparing the first ratio to a dataset of a plurality of fluids having a respective plurality of component ratios and determining the plus fraction using the comparison. The method includes quantifying at least one of the components in the fluid using the determined plus fraction.

In some embodiments, there is provided fluid analyzer for analyzing a fluid having a plurality of components. The fluid analyzer includes a gas chromatograph configured to obtain a sample of the fluid and determine a gas chromatogram, the gas chromatogram having a plus fraction. The fluid analyzer also includes a processor in communication with the gas chromatogram and configured to perform operations that include determining, from the gas chromatogram, a first ratio of a first at least one component of the first fluid to a second at least one component of the fluid and comparing the first ratio to a dataset of a plurality of fluids having a respective plurality of component ratios. The processer is further configured to perform operations that include determining the plus fraction using the comparison and quantifying at least one of the components in the fluid using the determined plus fraction.

In some embodiments, there is provided a method for analyzing a fluid having a plurality of components that includes obtaining a gas chromatogram of the fluid, the gas chromatogram having a plus fraction, and determining a fitting curve through the two or more relative concentrations of the fluid. The method further includes determining the plus fraction using the extrapolation of the fitting curve and quantifying at least one of the plurality components in the fluid using the determined plus fraction.

BRIEF DESCRIPTION OF THE DRAWINGS

Various aspects of this disclosure may be better understood upon reading the following detailed description and upon reference to the drawings in which.

DETAILED DESCRIPTION

Described herein are various embodiments for determining a plus fraction of a gas chromatogram. In some embodiments, a gas chromatogram may obtained, such as from a downhole gas chromatograph module of a fluid analysis tool. The plus fraction of the gas chromatogram may be determined using one or more of a ratiometric determination, fitting an exponential decay function, and fitting a probability density gamma function. The ratiometric determination may include selecting a ratio of components from the gas chromatogram and comparing the ratio to a dataset of known fluids having known plus fractions. The plus fraction of the gas chromatogram may be determined using the comparison. The determined plus fraction may be used to quantity components from the gas chromatogram.

In some embodiments, the exponential decay function may be fitted and extrapolated to infinity to determine the plus fraction above a specific carbon number. In some embodiments, the probably density gamma function may be fitted, and the plus fraction may be calculated by summing the percentages above a specific component and normalizing the summation to 100%. The determined plus fraction may be used to quantify components from the gas chromatogram. In some embodiments, an average plus fraction may be determined by calculating the average of plus fractions determined from two or more of a ratiometric determination, fitting an exponential decay function, and fitting a probability density gamma function.

These and other embodiments of the disclosure will be described in more detail through reference to the accompanying drawings in the detailed description of the disclosure that follows. This brief introduction, including section titles and corresponding summaries, is provided for the reader's convenience and is not intended to limit the scope of the claims or the proceeding sections. Furthermore, the techniques described above and below may be implemented in a number of ways and in a number of contexts. Several example implementations and contexts are provided with reference to the following figures, as described below in more detail. However, the following implementations and contexts are but a few of many.

Figure 1:
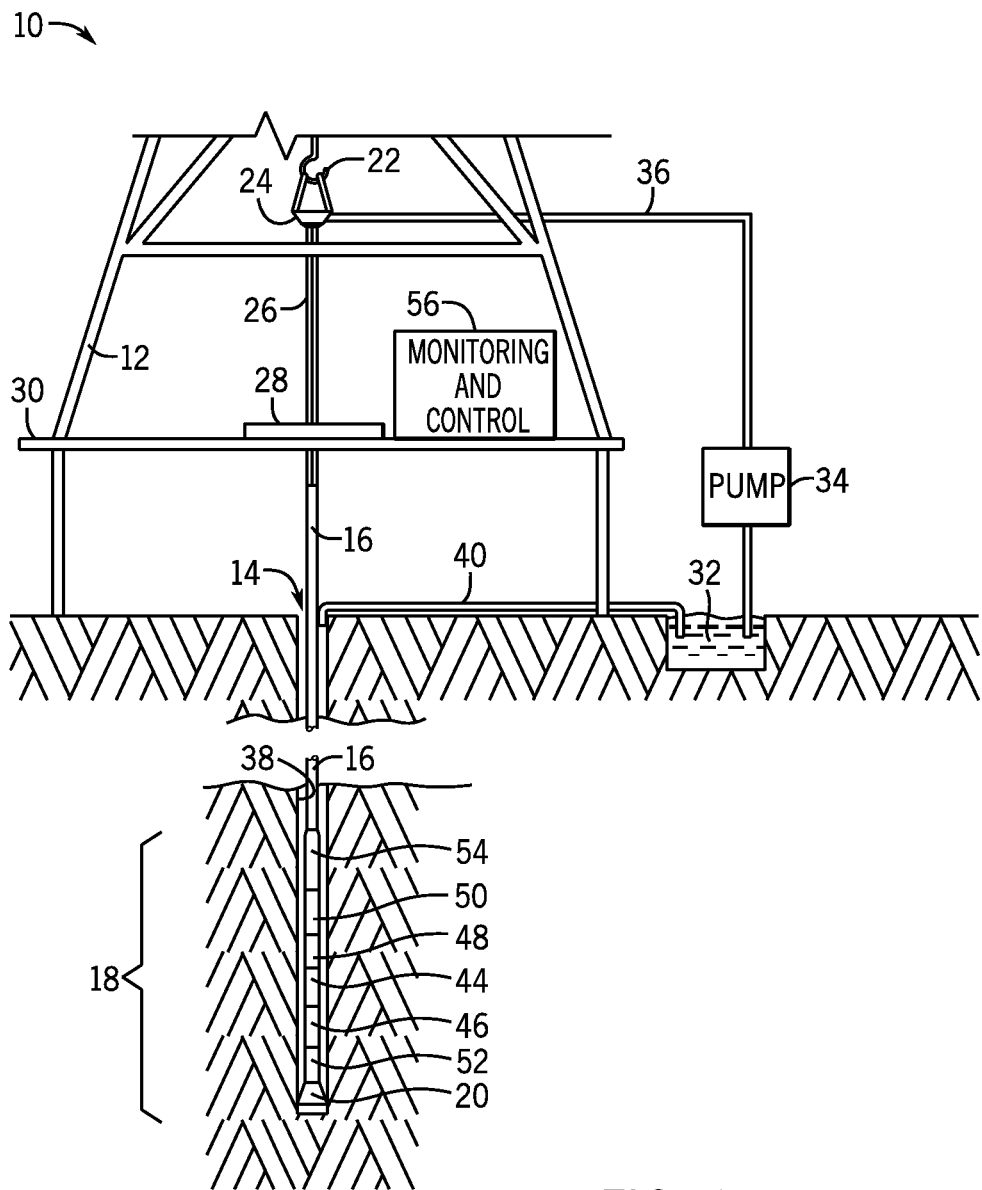
FIG. 1 is a schematic diagram of an example drilling system having a fluid sampling tool in a drill string in accordance with an embodiment of the present disclosure.

More specifically, a drilling system 10 is depicted in FIG. 1 in accordance with one embodiment. While certain elements of the drilling system 10 are depicted in this figure and generally discussed below, it will be appreciated that the drilling system 10 may include other components in addition to, or in place of, those presently illustrated and discussed. As depicted, the system 10 can include a drilling rig 12 positioned over a well 14. Although depicted as an onshore drilling system 10, it is noted that the drilling system could instead be an offshore drilling system. The drilling rig 12 can support a drill string 16 that includes a bottomhole assembly 18 having a drill bit 20. The drilling rig 12 can rotate the drill string 16 (and its drill bit 20) to drill the well 14.

The drill string 16 can be suspended within the well 14 from a hook 22 of the drilling rig 12 via a swivel 24 and a kelly 26. Although not depicted in FIG. 1, the skilled artisan will appreciate that the hook 22 can be connected to a hoisting system used to raise and lower the drill string 16 within the well 14. As one example, such a hoisting system could include a crown block and a drawworks that cooperate to raise and lower a traveling block (to which the hook 22 is connected) via a hoisting line. The kelly 26 can be coupled to the drill string 16, and the swivel 24 can allow the kelly 26 and the drill string 16 to rotate with respect to the hook 22. In the presently illustrated embodiment, a rotary table 28 on a drill floor 30 of the drilling rig 12 can be constructed to grip and turn the kelly 26 to drive rotation of the drill string 16 to drill the well 14. In other embodiments, however, a top drive system could instead be used to drive rotation of the drill string 16.

During operation, drill cuttings or other debris may collect near the bottom of the well 14. Drilling fluid 32, also referred to as drilling mud, can be circulated through the well 14 to remove this debris. The drilling fluid 32 may also clean and cool the drill bit 20 and provide positive pressure within the well 14 to inhibit formation fluids from entering the wellbore. In FIG. 1, the drilling fluid 32 can be circulated through the well 14 by a pump 34. The drilling fluid 32 can be pumped from a mud pit (or some other reservoir, such as a mud tank) into the drill string 16 through a supply conduit 36, the swivel 24, and the kelly 26. The drilling fluid 32 can exit near the bottom of the drill string 16 (e.g., at the drill bit 20) and can return to the surface through the annulus 38 between the wellbore and the drill string 16. A return conduit 40 can transmit the returning drilling fluid 32 away from the well 14. In some embodiments, the returning drilling fluid 32 can be cleansed (e.g., via one or more shale shakers, desanders, or desilters) and reused in the well 14. The drilling fluid 32 may include an oil-based mud (OBM) that may include synthetic muds, diesel-based muds, or other suitable muds.

In addition to the drill bit 20, the bottomhole assembly 18 can also include various instruments that measure information of interest within the well 14. For example, as depicted in FIG. 1, the bottomhole assembly 18 can include a logging-while-drilling (LWD) module 44 and a measurement-while-drilling (MWD) module 46. Both modules can include sensors, housed in drill collars, that can collect data and enable the creation of measurement logs in real-time during a drilling operation. The modules could also include memory devices for storing the measured data. The LWD module 44 can include sensors that measure various characteristics of the rock and formation fluid properties within the well 14. Data collected by the LWD module 44 could include measurements of gamma rays, resistivity, neutron porosity, formation density, sound waves, optical density, and the like. The MWD module 46 can include sensors that measure various characteristics of the bottomhole assembly 18 and the wellbore, such as orientation (azimuth and inclination) of the drill bit 20, torque, shock and vibration, the weight on the drill bit 20, and downhole temperature and pressure. The data collected by the MWD module 46 can be used to control drilling operations. The bottomhole assembly 18 can also include one or more additional modules 48, which could be LWD modules, MWD modules, or some other modules. It is noted that the bottomhole assembly 18 is modular, and that the positions and presence of particular modules of the assembly could be changed as desired. Further, as discussed in detail below, one or more of the modules 44, 46, and 48 can be or can include a fluid sampling tool configured to obtain a sample of a fluid from a subterranean formation and perform downhole fluid analysis to measure various properties of the sampled fluid. These properties may include an estimated density and/or optical density of the OBM filtrate, the sampled fluid, and other fluids. These and other estimated properties may be determined within or communicated to the LWD module 44, such as for subsequent utilization as input to various control functions and/or data logs.

The bottomhole assembly 18 can also include other modules. As depicted in FIG. 1 by way of example, such other modules can include a power module 50, a steering module 52, and a communication module 54. In one embodiment, the power module 50 can include a generator (such as a turbine) driven by flow of drilling mud through the drill string 16. In other embodiments, the power module 50 could also or instead include other forms of power storage or generation, such as batteries or fuel cells. The steering module 52 may include a rotary-steerable system that facilitates directional drilling of the well 14. The communication module 54 can enable communication of data (e.g., data collected by the LWD module 44 and the MWD module 46) between the bottomhole assembly 18 and the surface. In one embodiment, the communication module 54 can communicate via mud pulse telemetry, in which the communication module 54 uses the drilling fluid 32 in the drill string as a propagation medium for a pressure wave encoding the data to be transmitted.

The drilling system 10 can also include a monitoring and control system 56. The monitoring and control system 56 can include one or more computer systems that enable monitoring and control of various components of the drilling system 10. The monitoring and control system 56 can also receive data from the bottomhole assembly 18 (e.g., data from the LWD module 44, the MWD module 46, and the additional module 48) for processing and for communication to an operator, to name just two examples. While depicted on the drill floor 30 in FIG. 1, it is noted that the monitoring and control system 56 could be positioned elsewhere, and that the system 56 could be a distributed system with elements provided at different places near or remote from the well 14.

Figure 2:
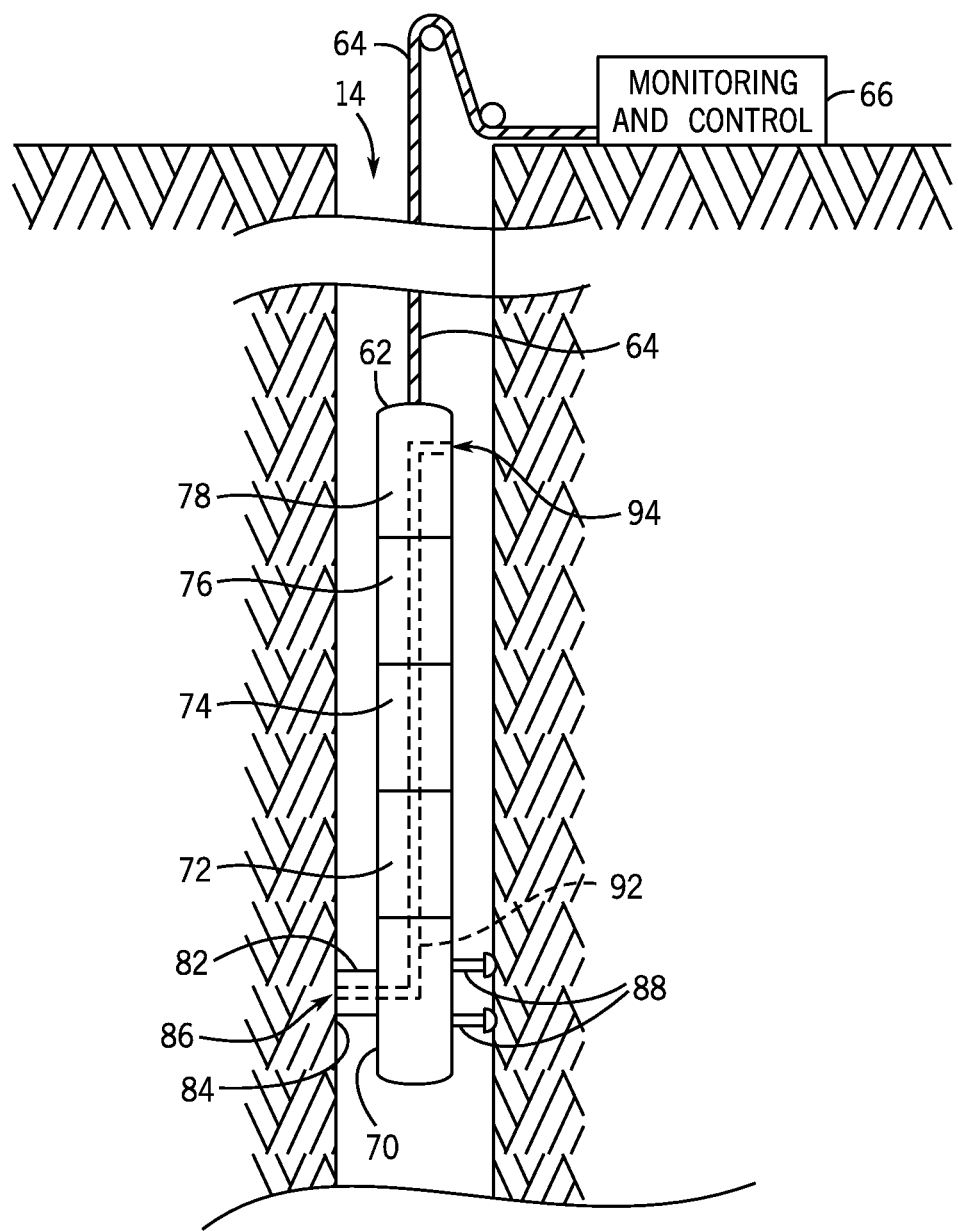
FIG. 2 is a schematic diagram of an example fluid sampling tool deployed within a well on a wireline in accordance with an embodiment of the present disclosure.

Another example of using a downhole tool for formation testing within the well 14 is depicted in FIG. 2. In this embodiment, a fluid sampling tool 62 can be suspended in the well 14 on a cable 64. The cable 64 may be a wireline cable with at least one conductor that enables data transmission between the fluid sampling tool 62 and a monitoring and control system 66. The cable 64 may be raised and lowered within the well 14 in any suitable manner. For instance, the cable 64 can be reeled from a drum in a service truck, which may be a logging truck having the monitoring and control system 66. The monitoring and control system 66 can control movement of the fluid sampling tool 62 within the well 14 and can receive data from the fluid sampling tool 62. In a similar fashion to the monitoring and control system 56 of FIG. 1, the monitoring and control system 66 may include one or more computer systems or devices and may be a distributed computing system. The received data can be stored, communicated to an operator, or processed, for instance. While the fluid sampling tool 62 is here depicted as being deployed by way of a wireline, in some embodiments the fluid sampling tool 62 (or at least its functionality) can be incorporated into or as one or more modules of the bottomhole assembly 18, such as the LWD module 44 or the additional module 48.

The fluid sampling tool 62 can take various forms. While it is depicted in FIG. 2 as having a body including a probe module 70, one or more fluid analysis modules 72, a pump module 74, a power module 76, and a fluid storage module 78, the fluid sampling tool 62 may include different modules in other embodiments. The probe module 70 can include a probe 82 that may be extended (e.g., hydraulically driven) and pressed into engagement against a wall 84 of the well 14 to draw fluid from a formation into the fluid sampling tool 62 through an intake 86. As depicted, the probe module 70 can also include one or more setting pistons 88 that may be extended outwardly to engage the wall 84 and push the end face of the probe 82 against another portion of the wall 84. In some embodiments, the probe 82 can include a sealing element or packer that isolates the intake 86 from the rest of the wellbore. In other embodiments, the fluid sampling tool 62 could include one or more inflatable packers that can be extended from the body of the fluid sampling tool 62 to circumferentially engage the wall 84 and isolate a region of the well 14 near the intake 86 from the rest of the wellbore. In such embodiments, the extendable probe 82 and setting pistons 88 could be omitted and the intake 86 could be provided in the body of the fluid sampling tool 62, such as in the body of a packer module housing an extendable packer.

The pump module 74 can draw the sampled formation fluid into the intake 86, through a flowline 92, and then either out into the wellbore through an outlet 94 or into a storage container (e.g., a bottle within fluid storage module 78) for transport back to the surface when the fluid sampling tool 62 is removed from the well 14. The one or more fluid analysis modules 72, which may also be referred to as a fluid analyzer 72 or a downhole fluid analysis (DFA) module, can include one more modules for measuring properties of the sampled formation fluid, and the power module 76 provides power to electronic components of the fluid sampling tool 62.

In some embodiments, the one or more fluids analysis modules 72 of the tool 62 include a gas chromatography (GC) module. The GC module is configured to determine a composition of the fluid sample and to provide an output signal indicative of the determined composition. The GC module may produce what may be referred to as a "gas chromatogram." For the example embodiment using gas chromatography, the gas chromatography module 116 is configured to obtain a chromatogram of sampled formation fluids available within the flowline 92 portion of the tool 62. An example of such a device is described in U.S. Pub. App. No. 2010/0018287, entitled "Wireline Downhole Gas Chromatograph and Downhole Gas Chromatography Method," and U.S. Pat. No. 7,384,453, entitled "Self Contained Chromatography System," each assigned to Schlumberger Technology Corporation and incorporated herein by reference in its entirety. In some embodiments, the GC module may output composition up to C9, e.g., hydrocarbon fractions C1 through C8. In some embodiments, the GC module may output composition up to C30, e.g., hydrocarbon fractions C1 through C29. Additionally, the GC module may also measure N2, CO2, and saturated and aromatic hydrocarbons and abundance ratios. In some embodiments, the GC module of the fluid analysis tool 62 described above may be insensitive to mud filtrate contamination in a sampled fluid by providing analysis of hydrocarbon fractions C1 through C8. Additionally, the GC module of the fluid analysis tool 62 may provide relatively fast profiling of fluid composition ratio changes versus depth.

The drilling and wireline environments depicted in FIGS. 1 and 2 are examples of environments in which a fluid sampling tool may be used to facilitate analysis of a downhole fluid. The presently disclosed techniques, however, could be implemented in other environments as well. For instance, the fluid sampling tool 62 may be deployed in other manners, such as by a slickline, coiled tubing, or a pipe string.

Accordingly, the embodiments described above and illustrated in FIGS. 1 and 2 may enable fluid sampling at different depths in the wellbore of the well 14. In some embodiments, systems depicted in FIGS. 1 and 2 may perform multiple fluid measurements by downhole sampling of reservoir fluid at one or more measurement stations (which may include or be referred to as downhole fluid analysis (DFA) stations) within the wellbore, conduct downhole fluid analysis of one or more reservoir fluid samples for each measurement station (including compositional analysis such as estimating concentrations of a plurality of compositional components of a given sample as well as other fluid properties) and, in some embodiments, relate the downhole fluid analysis to an Equation of State (EoS) model of the thermodynamic behavior of the fluid in order to characterize the reservoir fluid at different locations within the reservoir.

Figure 3:
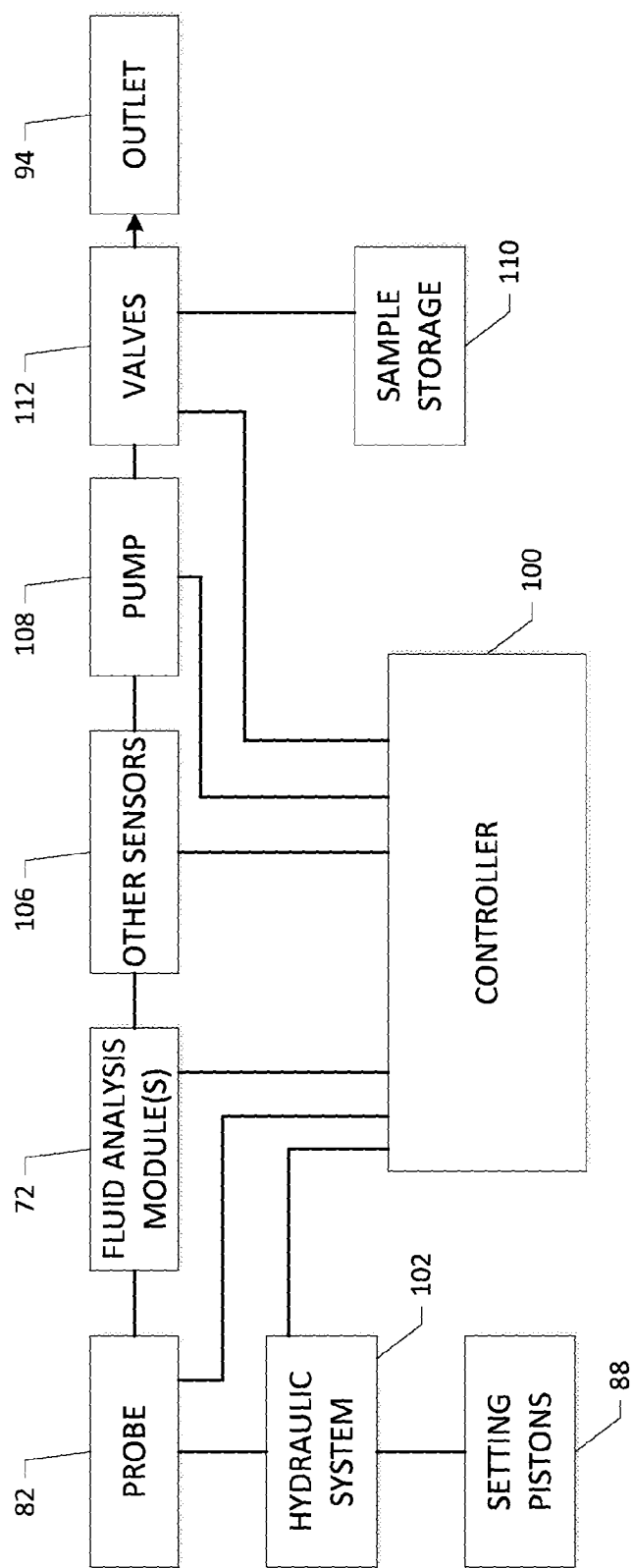
FIG. 3 is a block diagram of components of an example fluid sampling tool operated by a controller in accordance with an embodiment of the present disclosure.

Additional details as to the construction and operation of the fluid sampling tool 62 may be better understood through reference to FIG. 3. As shown in this figure, various components for carrying out functions of the fluid sampling tool 62 can be connected to a controller 100. The various components can include a hydraulic system 102 connected to the probe 82 and the setting pistons 88, the one or more fluid analysis modules 72 discussed above, one or more other sensors 106, a pump 108, and valves 112 for diverting sampled fluid into storage devices 110 rather than venting it through the outlet 94. The controller 100 may include or be coupled to an operator interface (not shown) that provides logs of predicted formation fluid properties that are accessible to an operator.

In operation, the hydraulic system 102 can extend the probe 82 and the setting pistons 88 to facilitate sampling of a formation fluid through the wall 84 of the well 14. It also can retract the probe 82 and the setting pistons 88 to facilitate subsequent movement of the fluid sampling tool 62 within the well. The one or more fluid analysis modules 72 can measure properties of the sampled formation fluid in accordance with the embodiments described above. For example, an optical analysis module may measure optical properties such as optical densities (absorbance) of the sampled formation fluid at different wavelengths of electromagnetic radiation. Using the optical densities, the composition of a sampled fluid (e.g., volume fractions of its constituent components) can be determined. In another example, as described above, a gas chromatography module may determine composition of the fluid sample and provide an output signal indicative of the determined composition. Other sensors 106 can be provided in the fluid sampling tool 62 (e.g., as part of the probe module 70 or the fluid analysis module 72) to take additional measurements related to the sampled fluid. In various embodiments, these additional measurements could include reservoir pressure and temperature, live fluid density, live fluid viscosity, electrical resistivity, saturation pressure, and fluorescence, to name several examples. In some embodiments, as mentioned above, some or all of other sensors 106 may be incorporated into a DFA module (e.g., such as in a PVT unit) of the fluid sampling tool 62.

Any suitable pump 108 may be provided in the pump module 74 to enable formation fluid to be drawn into and pumped through the flowline 92 in the manner discussed above. Storage devices 110 for formation fluid samples can include any suitable vessels (e.g., bottles) for retaining and transporting desired samples within the fluid sampling tool 62 to the surface. Both the storage devices 110 and the valves 112 may be provided as part of the fluid storage module 78.

In the embodiment depicted in FIG. 3, the controller 100 can facilitate operation of the fluid sampling tool 62 by controlling various components. Specifically, the controller 100 can direct operation (e.g., by sending command signals) of the hydraulic system 102 to extend and retract the probe 82 and the setting pistons 88 and of the pump 108 to draw formation fluid samples into and through the fluid sampling tool. The controller 100 can also receive data from the fluid analysis module 72 and the other sensors 106. This data can be stored by the controller 100 or communicated to another system (e.g., the monitoring and control system 56 or 66) for analysis. In some embodiments, the controller 100 is itself capable of analyzing the data it receives from the fluid analysis module(s) 72 and the other sensors 106. The controller 100 can also operate the valves 112 to divert sampled fluids from the flowline 92 into the storage devices 110.

A GC module of the fluid analysis tool 62 may provide relative concentrations (e.g., concentration ratios) of the components of the sampled fluid. As described below, embodiments of the disclosure may enable determination of the plus fraction of the gas chromatogram to provide for calculation of quantitative concentrations of the components in the fluid sample. As used herein, the term "plus fraction" refers to those components of the fluid that do not elute from the GC column. After determination of the plus fraction, the remaining components in the fluid may be quantified. The plus fraction may be determined using one or more of the techniques described below, such as using a ratiometric determination, using an exponential decay function, and using a gamma distribution function. In some embodiments, the plus fraction may by a C20+ fraction, a C22+ fraction, a C36+ fraction, or other plus fractions.

Figure 4:
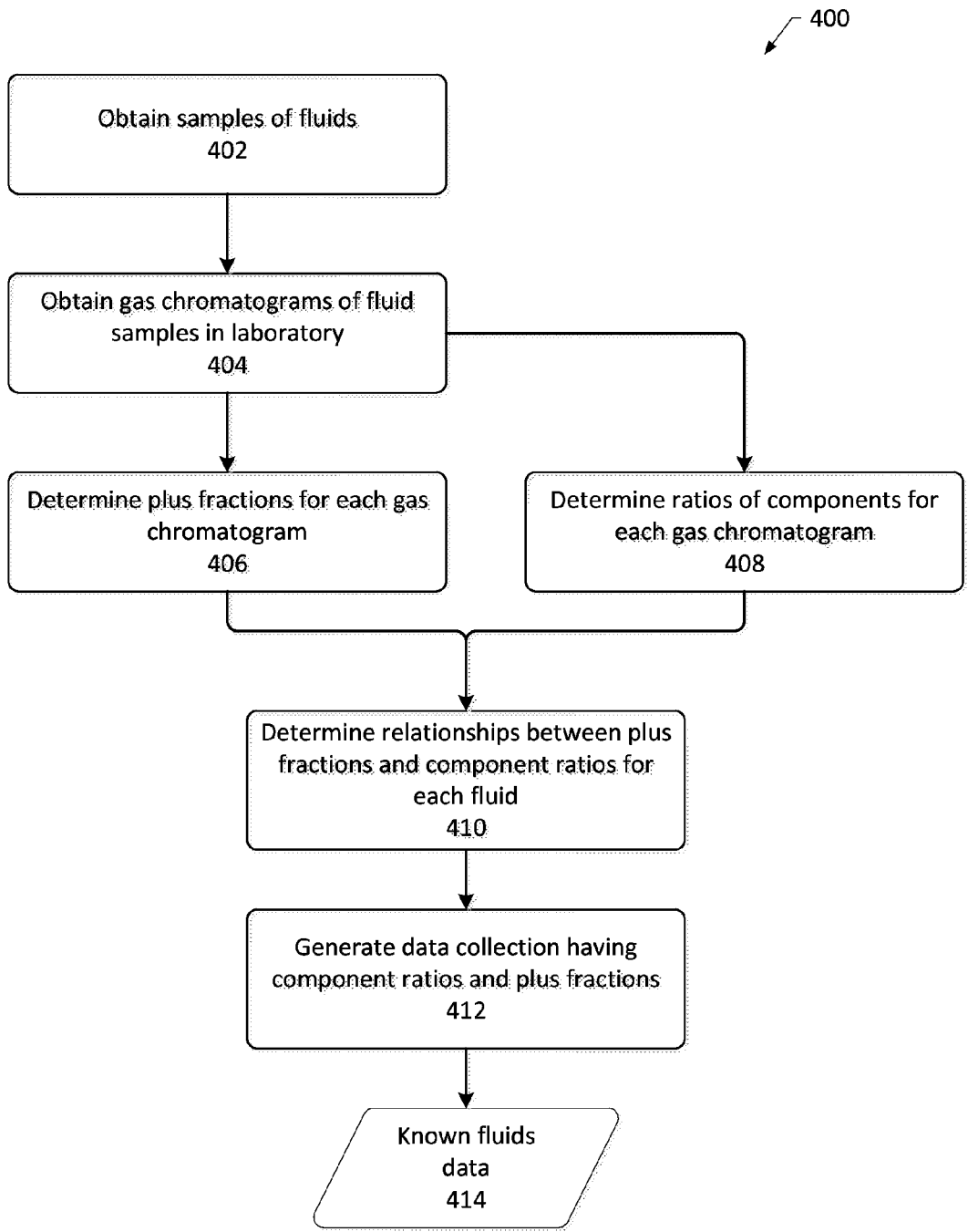
FIG. 4 is a block diagram of an example process for determining a relationship between component ratios and plus fractions of known fluids in accordance with an embodiment of the present disclosure.

FIG. 4 depicts a process 400 for determining relationships between component ratios and plus fractions of known fluids in accordance with an embodiment of the disclosure. Initially, fluid samples may be obtained (block 402) such as from existing wells. The sampled fluids may include, for example, dead oils, live oils or both. Next, laboratory gas chromatograms of the fluid samples may be obtained (block 404). For example, the fluid samples may be transported to a laboratory that provides detailed fluid analysis including gas chromatography.

Using suitable laboratory techniques, plus fractions for each gas chromatogram associated with each sampled fluid may be determined (block 406). For example, plus fractions associated with each sample fluid may be determined using an internal standard, absolute calibration, or other suitable techniques. In some embodiments, the quantification of components may omit components likely to be contaminated in the fluid. For example, in some embodiments lighter weight components below C15 may be omitted from the quantification determination. Additionally, as shown in FIG. 4, ratios of components in each gas chromatograph may be determined (block 408). For example, ratios of a carbon component to another carbon component may be determined, such as a concentration ratio of C22 to C16. In some embodiments, the ratios used for sampled fluids of dead oils may C15 and heavier components.

As shown in FIG. 4, relationships between component ratios and plus fractions for each fluid may be determined (block 410). For example, in the embodiment described above, the ratio of C22 to C16 of a fluid may be determined to have a relationship with a known plus fraction of a gas chromatogram for the fluid. In some embodiments, the plus fraction may be adjusted to account for lighter components that were omitted during the calculation (e.g., due to the omission of contaminated components described above).

Next, a data collection (such as a "dataset") having the component ratios and plus fractions may be generated (block 412). For example, the data collection may be a database or database table, a lookup table, a text file, or other suitable data collections. In some embodiments, the data collection may include an identifier for each fluid associated with the component ratio and determined plus fraction. The known fluids data collection 414 may be used in a ratiometric determination of a plus fraction for a downhole gas chromatograph as illustrated in FIG. 5 and described further below.

Figure 5:
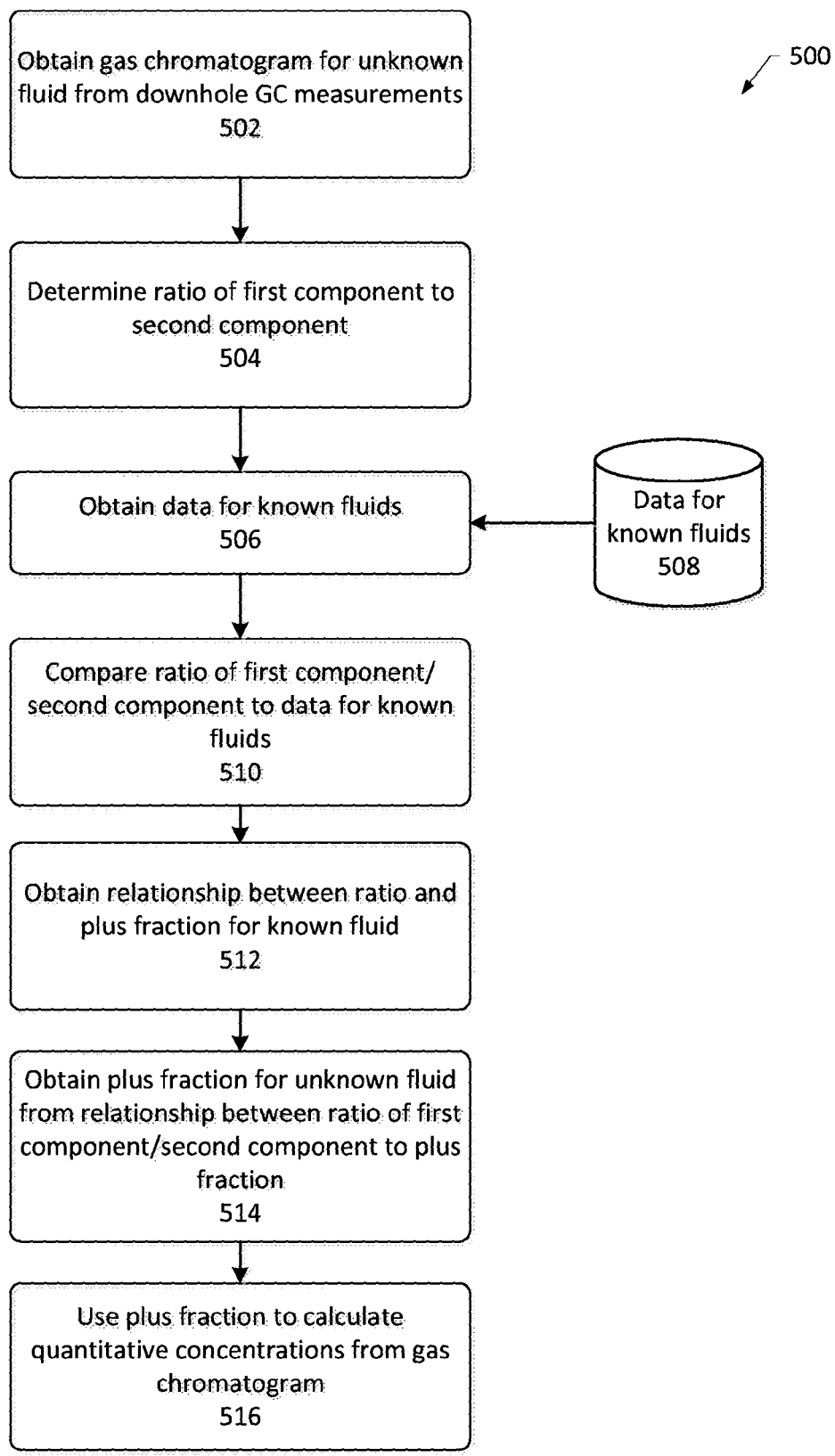
FIG. 5 is a block diagram of an example process for determining a plus fraction of a gas chromatogram using a ratiometric determination in accordance with an embodiment of the present disclosure.

FIG. 5 depicts a process 500 for determining a plus fraction of a gas chromatogram using a ratiometric determination in accordance with an embodiment of the disclosure. Initially, a gas chromatogram may be obtained from a downhole fluid analysis tool (block 502), such as the tool 62 described above. The concentration ratio of a first component to a second component in the gas chromatogram may be determined (block 504). In some embodiments, the components selected for a ratio may be separated by at least five carbon numbers, e.g., C22 to C16, C23 to C17, C21 to C15, and so on. In some embodiments, the components selected for a ratio may be selected to avoid possible contamination in the fluid sample. In some embodiments, components below C10 and components above C25 may not be selected for a component ratio. Next, data for known fluids may be obtained from a dataset 508 for known fluids (block 506).

As shown in FIG. 5, the concentration ratio of the first component to the second component may be compared to the data for known fluids (block 510). For example, the concentration ratio of the first component to the second component may be matched to a concentration ratio of the same components for a known fluid. The relationship between the concentration ratio for the known fluid and the plus fraction associated with the known fluid may be obtained from the known fluids data (block 512). The plus fraction for the gas chromatogram of the unknown fluid may be determined from the relationship between the concentration ratio and the plus fraction (block 514). For example, in some embodiments the ratio between C22 and C16 may be used to determine a C36+ fraction. The plus fraction may then be used to obtain quantitative concentrations for components in the gas chromatogram (block 516).

In some embodiments, multiple ratios of different components may be determined and matched to the known fluids dataset 508. For example, multiple ratios may be used, and an average of the plus fractions determined using each component ratio may be calculated for the plus fraction of the unknown fluids. In some embodiments, ratios of ranges of components may be used. For example, a concentration of C23 through C21 to C17 through C15 may be determined and matched to a ratio of the same component ranges in the known fluids dataset.

Figure 6:
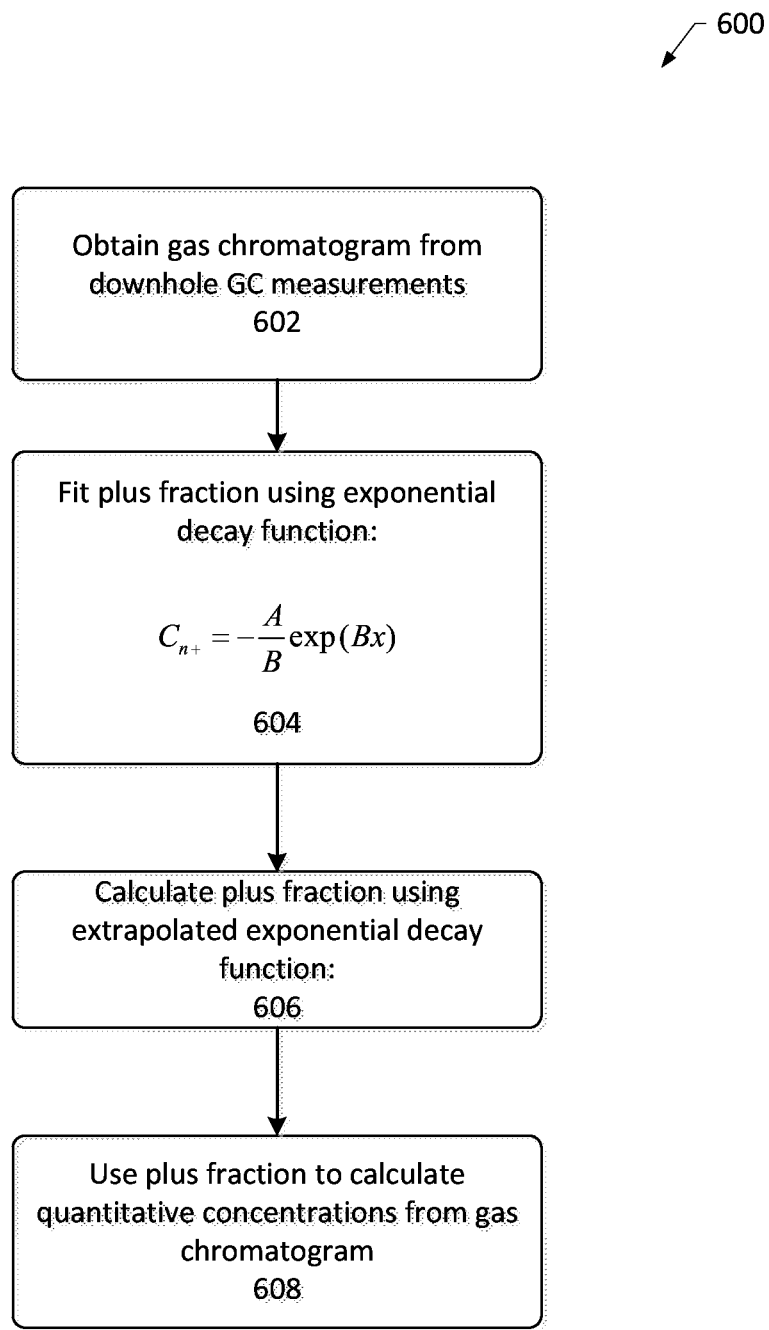
FIG. 6 is a block diagram of an example process for determining a plus fraction using an extrapolated exponential decay function in accordance with an embodiment of the present disclosure.

FIG. 6 depicts a process 600 for determining a plus fraction using an extrapolated exponential decay function in accordance with an embodiment of the disclosure. Initially, as described above, a gas chromatogram may be obtained from a downhole GC tool (block 602). As described below, exponential decay may be used to predict the size of the plus fraction based on the known mole fractions of the obtained gas chromatogram. The mole fractions of each carbon number ($C_x$) may be described by an exponential decay according to Equation 1 below:

$$C_x = A \exp(Bx) \quad (1)$$

Where $C_x$ is the mole fraction, x is the carbon number, and A and B are fitting parameters. The plus fraction ($C_{n+}$) may be determined according to the Equation 2 below:

$$C_{n+} = \frac{A}{B} \int_n^\infty \exp(Bx) \quad (2)$$

Extrapolating x to infinity results in Equation 3 below:

$$C_{n+} = -\frac{A}{B} \exp(Bx) \quad (3)$$

Thus, as shown in FIG. 6, an exponential decay function, such as that described above in Equation 3, may be fitted to relative concentrations of components from the gas chromatogram of the unknown fluid (block 604). The plus fraction may then be calculated using the extrapolated exponential decay function such as Equation 3 (block 606). The calculated plus fraction may be used to calculate the quantitative concentrations from the obtained gas chromatogram (block 608).

Figure 7:
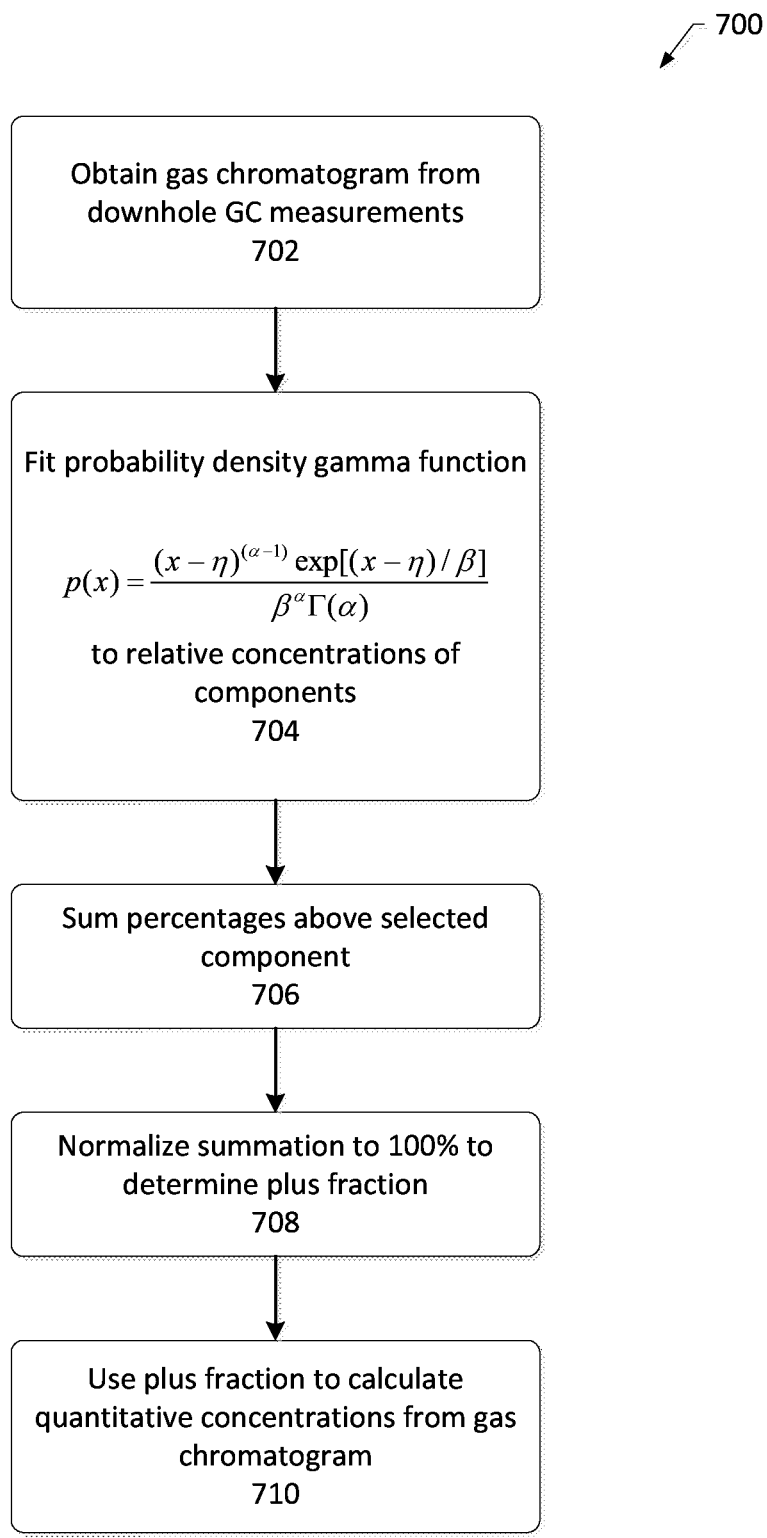
FIG. 7 is a block diagram of an example process for determining a plus fraction using a probability density gamma function in accordance with an embodiment of the present disclosure.

FIG. 7 depicts a process 700 for determining a plus fraction using a probability density gamma function in accordance with an embodiment of the disclosure. Initially, as described above, a gas chromatogram may be obtained from a downhole GC tool (block 702). The three-parameter gamma function shown below in Equation 4 may be used to describe a molar distribution of a plus fraction:

$$p(x) = \frac{(x-\eta)^{(\alpha-1)} \exp[(x-\eta)/\beta]}{\beta^\alpha \Gamma(\alpha)} \quad (4)$$

Where x is the carbon number, p(x) is the probably density, $\alpha$ and $\beta$ are curve-fitting parameters, and $\eta$ is an offset in carbon numbers. As shown FIG. 7, the probability density gamma function of Equation 4 may be fitted to relative concentrations (e.g., mole fractions) of components from the gas chromatogram of the unknown fluid. For example, $\alpha$, $\beta$, and $\eta$ may be varied to match known mole fractions of the components. Next, the plus fraction may be determined by summing the percentages above a selected component (block 606). For example, if a C36+ plus fraction is identified, the plus fraction may be determined by summing the percentages above C35. After summation, the summation may be normalized to 100% to determine the plus fraction (block 608).

In some embodiments, multiple plus fraction techniques described herein may be used in combination with each other. In some embodiments, an average plus fraction may be determined by calculating an average of a plus fraction determined using a ratiometric technique and a plus fraction determined using an exponential decay technique, an average of a plus fraction determined using a ratiometric technique and a plus fraction of determined using a probability density gamma function, or an average of a plus fraction determined using an exponential decay function and a plus fraction determined using a probability density gamma function. In some embodiments, an average plus fraction may be determined by calculating an average of a plus fraction determined using a ratiometric technique, a plus fraction determined using an exponential decay technique, and a plus fraction determined using a probability density gamma function. In some embodiments, the accuracy of the plus fraction determinations of a relatively lighter plus fraction (e.g., C21+) may be improved by the use of lighter components in the gas chromatogram (e.g., components below C11).

In some embodiments, the difference between plus fractions determined using the techniques described above may be used. For example, in some embodiments the difference between a plus fraction determined using a ratiometric technique and a plus fraction determined using an exponential decay function may be compared to a threshold value. If the difference is greater than the threshold, more detailed analysis of a fluid (or fluid sample) may be performed. In some embodiments, the difference between a plus fraction determined using a ratiometric technique and a plus fraction determined using a probability density gamma function, or the difference between a plus fraction determined using an exponential decay function and a plus fraction determined using a probability density gamma function, may be used in a similar manner.

Figure 8:
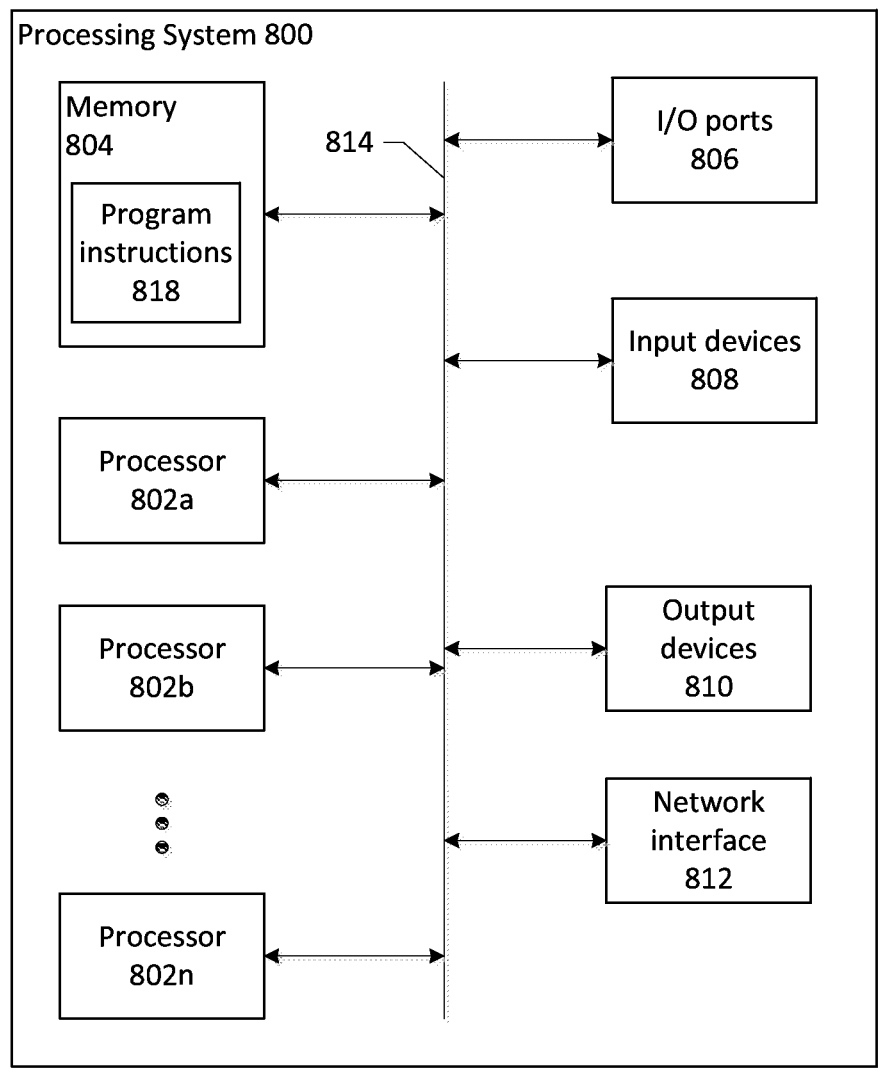
FIG. 8 is a block diagram of an example processing system in accordance with an embodiment of the present disclosure.

FIG. 8 is a block diagram of further details of an example processing system 800 (e.g., processing system 38) that may execute example machine-readable instructions used to implement one or more of processes described herein and, in some embodiments, to implement a portion of one or more of the example downhole tools described herein. The processing system 800 may be or include, for example, controllers (e.g., controller 100), special-purpose computing devices, servers, personal computers, personal digital assistant (PDA) devices, tablet computers, wearable computing devices, smartphones, internet appliances, and/or other types of computing devices. Moreover, while it is possible that the entirety of the system 800 shown in FIG. 8 is implemented within a downhole tool, it is also contemplated that one or more components or functions of the system 800 may be implemented in wellsite surface equipment. As shown in the embodiment illustrated in FIG. 8, the processing system 800 may include one or more processors (e.g., processors 802A-802N), a memory 804, I/O ports 806 input devices 808, output devices 810, and a network interface 812. The process system 800 may also include one or more additional interfaces 814 to facilitate communication between the various components of the system 800.

The processor 802 may provide the processing capability to execute programs, user interfaces, and other functions of the system 800. The processor 802 may include one or more processors and may include "general-purpose" microprocessors, special purpose microprocessors, such as application-specific integrated circuits (ASICs), or any combination thereof. In some embodiments, the processor 802 may include one or more reduced instruction set (RISC) processors, such as those implementing the Advanced RISC Machine (ARM) instruction set. Additionally, the processor 802 may include single-core processors and multicore processors and may include graphics processors, video processors, and related chip sets. Accordingly, the system 800 may be a uni-processor system having one processor (e.g., processor 802a), or a multi-processor system having two or more suitable processors (e.g., 802A-802N). Multiple processors may be employed to provide for parallel or sequential execution of the techniques described herein. Processes, such as logic flows, described herein may be performed by the processor 802 executing one or more computer programs to perform functions by operating on input data and generating corresponding output. The processor 802 may receive instructions and data from a memory (e.g., memory 804).

The memory 804 (which may include one or more tangible non-transitory computer readable storage mediums) may include volatile memory and non-volatile memory accessible by the processor 802 and other components of the system 800. For example, the memory 804 may include volatile memory, such as random access memory (RAM). The memory 804 may also include non-volatile memory, such as ROM, flash memory, a hard drive, other suitable optical, magnetic, or solid-state storage mediums or any combination thereof. The memory 804 may store a variety of information and may be used for a variety of purposes. For example, the memory 804 may store executable computer code, such as the firmware for the system 800, an operating system for the system 800, and any other programs or other executable code for providing functions of the system 800. Such executable computer code may include program instructions 818 executable by a processor (e.g., one or more of processors 802A-802N) to implement one or more embodiments of the present disclosure, such as determining GOR in accordance with the techniques described above. Program instructions 818 may include computer program instructions for implementing one or more techniques described herein. Program instructions 818 may include a computer program (which in certain forms is known as a program, software, software application, script, or code).

The interface 814 may include multiple interfaces and may enable communication between various components of the system 800, the processor 802, and the memory 804. In some embodiments, the interface 814, the processor 802, memory 804, and one or more other components of the system 800 may be implemented on a single chip, such as a system-on-a-chip (SOC). In other embodiments, these components, their functionalities, or both may be implemented on separate chips. The interface 814 may enable communication between processors 802a-802n, the memory 804, the network interface 812, or any other devices of the system 800 or a combination thereof. The interface 814 may implement any suitable types of interfaces, such as Peripheral Component Interconnect (PCI) interfaces, the Universal Serial Bus (USB) interfaces, Thunderbolt interfaces, Firewire (IEEE-1394) interfaces, and so on.

The system 800 may also include an input and output port 806 to enable connection of additional devices, such as I/O devices 808, 810. Embodiments of the present disclosure may include any number of input and output ports 806, including headphone and headset jacks, universal serial bus (USB) ports, Firewire (IEEE-1394) ports, Thunderbolt ports, and AC and DC power connectors. Further, the system 800 may use the input and output ports to connect to and send or receive data with any other device, such as other portable computers, personal computers, printers, etc.

The processing system 800 may include one or more input devices 808. The input device(s) 808 permit a user to enter data and commands used and executed by the processor 802. The input device 808 may include, for example, a keyboard, a mouse, a touchscreen, a track-pad, a trackball, an isopoint, and/or a voice recognition system, among others. The processing system 800 may also include one or more output devices 810. The output devices 810 may include, for example, display devices (e.g., a liquid crystal display or cathode ray tube display (CRT), among others), printers, and/or speakers, among others.

The system 800 depicted in FIG. 8 also includes a network interface 812. The network interface 812 may include a wired network interface card (NIC), a wireless (e.g., radio frequency) network interface card, or combination thereof. The network interface 812 may include known circuitry for receiving and sending signals to and from communications networks, such as an antenna system, an RF transceiver, an amplifier, a tuner, an oscillator, a digital signal processor, a modem, a subscriber identity module (SIM) card, memory, and so forth. The network interface 812 may communicate with networks (e.g., network 816), such as the Internet, an intranet, a cellular telephone network, a wide area network (WAN), a local area network (LAN), a metropolitan area network (MAN), or other devices by wired or wireless communication using any suitable communications standard, protocol, or technology.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language is not generally intended to imply that features, elements, and/or operations are in any way used for one or more implementations or that one or more implementations necessarily include logic for deciding, with or without user input or prompting, whether these features, elements, and/or operations are included or are to be performed in any particular implementation.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims. Although specific terms are employed herein, they are used in a generic and descriptive sense and not for purposes of limitation.

What is claimed is:

1. A method for analyzing a fluid having a plurality of components, comprising:

obtaining a gas chromatogram of the fluid, the gas chromatogram comprising a plus fraction;
determining, from the gas chromatogram, a first ratio of a first at least one component of the fluid to a second at least one component of the fluid;
comparing the first ratio to a dataset of a plurality of fluids having a respective plurality of component ratios;
determining the plus fraction using the comparison; and
quantifying at least one of the components in the fluid using the determined plus fraction.

2. The method of claim 1, wherein the gas chromatogram is obtained from a downhole gas chromatograph inserted into a well and configured to generate the gas chromatogram from a sample of the first fluid.

3. The method of claim 1, wherein the first at least one component comprises C22 and the second at least one component comprises C16.

4. The method of claim 1, comprising wherein the plus fraction comprises a C20+ fraction.

5. The method of claim 1, wherein the first at least one component and the second at least one component are separated by at least five carbon numbers.

6. The method of claim 1, comprising:
determining the plus fraction by extrapolating an exponential decay function or by fitting a probability density gamma function to produce a second determined plus fraction.

7. The method of claim 6, comprising:
calculating an average of the determined plus fraction and the second determined plus fraction to determine an averaged plus fraction; and
quantifying at least one of the plurality components in the fluid using the averaged plus fraction.

8. The method of claim 1, wherein the dataset comprises relationships between the plurality of component ratios and a respective plurality of known plus fractions.

9. A fluid analyzer for analyzing a fluid having a plurality of components, comprising:
a gas chromatograph configured to obtain a sample of the fluid and determine a gas chromatogram, the gas chromatogram comprising a plus fraction;
one or more processors in communication with the gas chromatogram and configured to perform operations comprising:
determining, from the gas chromatogram, a first ratio of a first at least one component of the fluid to a second at least one component of the fluid;
comparing the first ratio to a dataset of a plurality of fluids having a respective plurality of component ratios;
determining the plus fraction using the comparison; and
quantifying at least one of the components in the fluid using the determined plus fraction.

10. The fluid analyzer of claim 9, wherein the first at least one component comprises C22 and the second at least one component comprises C16.

11. The fluid analyzer of claim 9, comprising wherein the plus fraction comprises a C36+ fraction.

12. The fluid analyzer of claim 9, wherein the first at least one component and the second at least one component are separated by at least five carbon numbers.

13. The fluid analyzer of claim 9, comprising:
determining the plus fraction by extrapolating an exponential decay function or by fitting a probability density gamma function to produce a second determined plus fraction.

14. The fluid analyzer of claim 13, comprising:
calculating an average of the determined plus fraction and the second determined plus fraction to determine an averaged plus fraction; and
quantifying at least one of the plurality components of the first fluid using the averaged plus fraction.

15. The fluid analyzer of claim 9, wherein the dataset comprises relationships between the plurality of component ratios and a respective plurality of known plus fractions.

16. A method for analyzing a fluid having a plurality of components, comprising:
obtaining a gas chromatogram of the fluid, the gas chromatogram comprising a plus fraction;
determining a fitting curve through the two or more relative concentrations of the fluid;
determining the plus fraction using the extrapolation of the fitting curve; and
quantifying at least one of the plurality components in the fluid using the determined plus fraction.

17. The method of claim 16, wherein the fitting curve is an exponential decay function.

18. The method of claim 16, wherein the fitting curve is a probability density gamma function.

19. The method of claim 16, wherein the gas chromatogram is obtained from a downhole gas chromatograph inserted into a well and configured to generate the gas chromatogram from a sample of the fluid.

20. The method of claim 16, comprising wherein the plus fraction comprises a C20+ fraction.

* * * * *